(12) United States Patent
Haas et al.

(10) Patent No.: US 8,791,047 B2
(45) Date of Patent: Jul. 29, 2014

(54) PLANT GROWTH REGULATION

(75) Inventors: Ulrich Johannes Haas, Basel (DE); Tyler L Harp, Stein (CH)

(73) Assignee: Syngenta Participations AG, Basel (CH)

( * ) Notice: Subject to any disclaimer, the term of this patent is extended or adjusted under 35 U.S.C. 154(b) by 121 days.

(21) Appl. No.: 13/512,315

(22) PCT Filed: Nov. 24, 2010

(86) PCT No.: PCT/EP2010/007128
§ 371 (c)(1),
(2), (4) Date: Jun. 20, 2013

(87) PCT Pub. No.: WO2011/063946
PCT Pub. Date: Jun. 3, 2011

(65) Prior Publication Data
US 2013/0303372 A1    Nov. 14, 2013

(30) Foreign Application Priority Data
Nov. 27, 2009   (GB) .................................. 0920893.5

(51) Int. Cl.
*A01N 25/26*  (2006.01)
*A01N 37/00*  (2006.01)
*A01N 37/10*  (2006.01)

(52) U.S. Cl.
USPC ........................... 504/100; 504/142; 504/144

(58) Field of Classification Search
None
See application file for complete search history.

(56) References Cited

U.S. PATENT DOCUMENTS 6,114,284 A * 9/2000 Fujisawa et al. .............. 504/140
2007/0149401 A1 * 6/2007 Haskell et al. ................ 504/103

FOREIGN PATENT DOCUMENTS

| DE | 263914 | * | 1/1989 |
| DE | 2639145 | | 1/1989 |
| EP | 686343 | * | 2/1994 |
| EP | 0686343 | | 12/1995 |
| WO | 2005102047 | | 11/2005 |
| WO | 2005107436 | | 11/2005 |

* cited by examiner

*Primary Examiner* — Alton Pryor
(74) *Attorney, Agent, or Firm* — R. Kody Jones

(57) ABSTRACT

The present invention relates to a method for improving the plant growth regulation of and/or enhancing crop plants, by applying to the crop plants a mixture of a plant growth regulator, and jasmonic acid or a salt or ester thereof.

11 Claims, No Drawings

PLANT GROWTH REGULATION

This application is a 371 of International Application No. PCT/EP2010/007128 filed Nov. 24, 2010, which claims priority to GB 0920893.5 filed Nov. 27, 2009, the contents of which are incorporated herein by reference.

The present invention relates to a method for improving the plant growth regulation of crop plants, by applying to the crop plants a mixture of a plant growth regulator, and jasmonic acid or a salt or ester thereof.

Plant growth regulators are often used to regulate the growth and development of crop plants. For example, plant growth regulators are used to slow the development of a crop (such as oil seed rape) so that it flowers at a desired time, reduce the height of a crop (such as in cereals) so that it is less susceptible to lodging, increase nitrogen efficiency, regulate flowering and fruit set of a crop (such as fruit trees), and slow turfgrass growth rate to reduce mowing frequency.

There are several different classes of plant growth regulator. Known classes include azoles (such as uniconazole, and paclobutrazol), cyclohexane carboxylates (such as trinexapac-ethyl, and prohexadione-calcium), pyrimidinyl carbinols (such as flurprimidol, and ancymidol), quarternary ammoniums (such as chlormequat-chloride, and mepiquat-chloride), and sulphonyl-amino phenyl-acetamides (such as mefluidide).

Plant growth regulators operate by various modes of action. For example, onium-type plant growth retardants such as chlormequat-chloride and mepiquat-chloride, that possess a positively charged ammonium, phosphonium or sulphonium group, function by blocking the synthesis of gibberellin early in the biosynthetic pathway. Growth retardants comprising a nitrogen-containing heterocycle, such as flurprimidol, paclobutrazol and uniconazole-P, act as inhibitors of monooxygenases that catalyse oxidative steps in gibberellin biosynthesis. Structural mimics of 2-oxoglutaric acid, such as the acylcyclohexanediones trinexapac-ethyl and prohexadione-calcium, interfere with the late steps of gibberellin biosynthesis. Other plant growth regulators, such as mefluidide, inhibit cell division and differentiation.

Plant growth regulators such as trinexapac-ethyl are commonly used on crops to reduce the risk of lodging through stem thickening and shortening, and improved rooting.

In some cases, active ingredients have been shown to be more effective when mixed with other active ingredients compared to when applied individually, and this is referred to as "synergism", since the combination demonstrates a potency or activity level exceeding that which it would be expected to have based on knowledge of the individual potencies of the components.

The present invention resides in the discovery that plant growth regulators exhibit an improved plant growth regulation effect when applied in combination with jasmonic acid, or salts of esters thereof.

The present invention is also useful in providing a plant growth regulation effect in crop plants that is as good as, or better than, that achieved using existing plant growth regulating products, using a lower concentration of any one plant growth regulator. This enables the composition to be applied at an earlier growth stage of the crop plants without causing phytotoxicity.

According to the present invention, there is provided a method for regulating the growth of crop plants, comprising applying to the plants, plant parts, plant propagation material, or a plant growing locus, a plant growth regulator and jasmonic acid or a salt or ester thereof, in a synergistically effective amount, wherein the crop plants are cereals, sugar cane, rice or corn.

The term 'regulating the growth' includes restricting shoot growth, promoting root growth, stunting, and the like.

The term 'plants' refers to all physical parts of a plant, including seeds, seedlings, saplings, roots, tubers, stems, stalks, foliage and fruits.

The term 'plant propagation material' denotes generative parts of the plant, such as seeds, which can be used for the multiplication of the latter, and vegetative material, such as cuttings or tubers, for example potatoes. In particular, it includes seeds (in the strict sense), roots, fruits, tubers, bulbs, rhizomes and parts of plants. Germinated plants and young plants which are to be transplanted after germination or after emergence from the soil, may also be mentioned—these young plants may be protected before transplantation by a total or partial treatment by immersion. Suitably "plant propagation material" is understood to denote seeds.

The term 'plant growing locus' is intended to embrace the place on which the plants are growing, where the plant propagation materials of the plants are sown or where the plant propagation materials of the useful plants will be placed into the soil. An example for such a locus is a field, on which crop plants are growing.

The present invention also provides a method for enhancing crop plants, comprising applying to the plants, plant parts, plant propagation material, or a plant growing locus, a plant growth regulator and jasmonic acid or a salt or ester thereof in a synergistically effective amount. In one embodiment, the crop is not turfgrass.

According to the present invention, 'enhancing crop plants' means an improving plant vigour and/or tolerance to stress factors, either of which may lead to increased yield. In one embodiment, the present invention relates to a method for improving plant yield, comprising applying to the plant, plant part, plant propagation material, or a plant growing locus, a plant growth regulator and jasmonic acid or a salt or ester thereof. Such improved yield may be as a result of improved root growth. In a further embodiment, the present invention relates to a method for improving plant vigour and/or plant tolerance to stress factors, comprising applying to the plant, plant part, plant propagation material, or a plant growing locus, a plant growth regulator and jasmonic acid or a salt or ester thereof.

According to the present invention, an improvement in plant vigour means that certain traits are improved qualitatively or quantitatively when compared with the same trait in a control plant which has been grown under the same conditions in the absence of the method of the invention. Such traits include, but are not limited to, early and/or improved germination, improved emergence, the ability to use less seeds, increased root growth, a more developed root system, increased shoot growth, increased tillering, stronger tillers, more productive tillers, increased or improved plant stand, less plant verse (lodging), an increase and/or improvement in plant height, an increase in plant weight (fresh or dry), bigger leaf blades, increased photosynthetic activity, earlier flowering, homogenous flowering, longer panicles, early grain maturity, increased seed, fruit or pod size, increased pod or ear number, increased seed number per pod or ear, increased seed mass, enhanced seed filling, less dead basal leaves, delay of senescence, improved vitality of the plant and/or less inputs needed (e.g. less fertiliser, water and/or labour needed). A plant with improved vigour may have an increase in any of the aforementioned traits or any combination or two or more of the aforementioned traits. Suitably, the method of the present invention increases plant height, plant weight and/or provides enhanced germination.

An improvement in plant quality may be observed, meaning that certain traits are improved qualitatively or quantitatively when compared with the same trait in a control plant which has been grown under the same conditions in the absence of the method of the invention. Such traits include, but are not limited to, improved visual appearance of the plant (e.g. improved colour, density, uniformity, compactness), reduced ethylene (reduced production and/or inhibition of reception), improved quality of harvested material, e.g. seeds, fruits, leaves, vegetables (such improved quality may manifest as improved visual appearance of the harvested material, improved carbohydrate content (e.g. increased quantities of sugar and/or starch, improved sugar acid ratio, reduction of reducing sugars, increased rate of development of sugar), improved protein content, improved oil content and composition, improved nutritional value, reduction in anti-nutritional compounds, improved organoleptic properties (e.g. improved taste) and/or improved consumer health benefits (e.g. increased levels of vitamins and anti-oxidants)), improved post-harvest characteristics (e.g. enhanced shelf-life and/or storage stability, easier processability, easier extraction of compounds) and/or improved seed quality (e.g. for use in following seasons). A plant with improved quality may have an increase in any of the aforementioned traits or any combination or two or more of the aforementioned traits.

According to the present invention, an improved tolerance to stress factors means that certain traits are improved qualitatively or quantitatively when compared with the same trait in a control plant which has been grown under the same conditions in the absence of the method of the invention. Such traits include, but are not limited to, an increased tolerance and/or resistance to abiotic stress factors which cause sub-optimal growing conditions such as drought (e.g. any stress which leads to a lack of water content in plants, a lack of water uptake potential or a reduction in the water supply to plants), cold exposure, heat exposure, osmotic stress, UV stress, flooding, increased salinity (e.g. in the soil), increased mineral exposure, ozone exposure, high light exposure and/or limited availability of nutrients (e.g. nitrogen and/or phosphorus nutrients). A plant with improved tolerance to stress factors may have an increase in any of the aforementioned traits or any combination or two or more of the aforementioned traits. In the case of drought and nutrient stress, such improved tolerances may be due to, for example, more efficient uptake, use or retention of water and nutrients. Suitably, the method of the present invention increases tolerance of plants to drought.

Any or all of the above crop enhancements may lead to an improved yield by improving e.g. plant physiology, plant growth and development and/or plant architecture. In the context of the present invention 'yield' includes, but is not limited to, (i) an increase in biomass production, grain yield (e.g. grain size, grain number, grain density), starch content, oil content and/or protein content, which may result from (a) an increase in the amount produced by the plant per se or (b) an improved ability to harvest plant matter, (ii) an improvement in the composition of the harvested material (e.g. improved sugar acid ratios, improved oil composition, increased nutritional value, reduction of anti-nutritional compounds, increased consumer health benefits) and/or (iii) an increased/facilitated ability to harvest the crop, improved processability of the crop and/or better storage stability/shelf life. Increased yield of an agricultural plant means that, where it is possible to take a quantitative measurement, the yield of a product of the respective plant is increased by a measurable amount over the yield of the same product of the plant produced under the same conditions, but without application of the present invention. According to the present invention, it is preferred that the yield be increased by at least 0.5%, more preferred at least 1%, even more preferred at least 2%, still more preferred at least 4%, preferably 5% or even more.

Any or all of the above crop enhancements may also lead to an improved utilisation of land, i.e. land which was previously unavailable or sub-optimal for cultivation may become available. For example, plants which show an increased ability to survive in drought conditions, may be able to be cultivated in areas of sub-optimal rainfall, e.g. perhaps on the fringe of a desert or even the desert itself.

The term 'synergistically effective amount' indicates the quantity of such compounds which is capable of modifying the effect on the growth of plants, where said effect is greater than the sum of the effects obtained by applying each of the compounds individually.

Jasmonic acid is a plant hormone that acts as a signalling compound to induce the production of phytoalexins that protect against herbivory, fungal invasion, and to induce enzymatic antioxidant activity such as superoxide dismutase and catalases. Jasmonic acid is also thought to regulate plant growth when used at low rates by increasing the total phenolic content of leaves, and therefore inducing free radical buffering capacity and reducing shoot growth.

Various derivatives of jasmonic acid are known. For example, the methyl ester of jasmonic acid (methyl jasmonate, MeJA), methyl (1R,2R)-3-Oxo-2-(2Z)-2-pentenyl-cyclopentaneacetate, has the formula

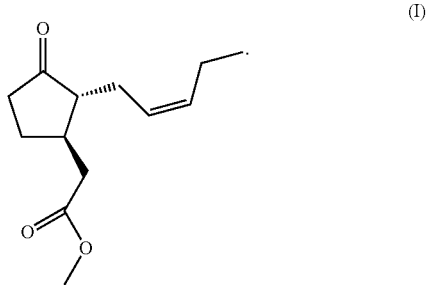 [SMILES: CC/C=C\C[C@H]1C(=O)CC[C@@H]1CC(=O)OC]

(I)

Reference to the term 'jasmonic acid' herein, includes reference to salts, esters or derivatives of jasmonic acid. In one embodiment of the present invention, the methyl ester of jasmonic acid, methyl jasmonate, is used.

Any plant growth regulator may be used in accordance with the present invention. A complete list of all commercially available plant growth regulators may be obtained from the Pesticide Manual (14$^{th}$ edition, published by the British Crop Protection Council). In one embodiment, the plant growth regulator is selected from the group consisting of trinexapac-ethyl, prohexadione-calcium, paclobutrazol, uniconazole, flurprimidol, mefluidide, mepiquat-chloride, chlormequat-chloride, and a mixture thereof.

Suitably, the plant growth regulator is a gibberellin biosynthesis inhibitor. Suitably, the plant growth regulator is a class A gibberellin biosynthesis inhibitor. Suitably, the plant growth regulator is a class B gibberellin biosynthesis inhibitor. In a preferred embodiment the plant growth regulator is trinexapac-ethyl, prohexadione-calcium or chlormequat-chloride. In one embodiment, the plant growth regulator is trinexapac-ethyl. In one embodiment, the plant growth regulator is prohexadione-calcium. In one embodiment, the plant growth regulator is chlormequat-chloride. In one embodiment, the plant growth regulator is paclobutrazol. In one embodiment, the plant growth regulator is flurprimidol.

If desired, it is possible to use more than one plant growth regulator in combination, in accordance with the present invention, such as mixtures of trinexapac-ethyl and paclobutrazol.

In the present invention, the mixture ratio of plant growth regulator to jasmonic acid at which the growth regulation effect is synergistic lies within the range from about 1:1000 to about 1000:1 by weight. Suitably, the mixture ratio of plant growth regulator to jasmonic acid is from about 1:100 to about 100:1 by weight. More suitably, the mixture ratio of plant growth regulator to jasmonic acid is from about 5:1 to about 1:20 by weight. For example, where the plant growth regulator is trinexapac-ethyl and the jasmonic acid derivative is methyl jasmonate, a mixture ratio from about 1:1 to about 1:10 by weight is preferred.

The rate of application of the compounds of the present invention may vary within wide limits and depends upon the nature of the soil, the method of application, the target insect pest to be controlled, the prevailing climatic conditions, and other factors governed by the method of application and the time of application. The compounds of the present invention are generally applied at a rate of 0.001 to 4 kg/ha, especially from 0.005 to 1 kg/ha, in particular of 0.01 to 0.5 kg/ha. Suitably, the plant growth regulator is applied at a rate from about 50 to about 100 g ai/ha, and jasmonic acid is applied at a rate from about 100 to about 400 g ai/ha. When the plant growth regulator is trinexapac-ethyl, a particularly preferred rate is 100 g ai/ha. When the jasmonic acid is in the form of methyl jasmonate, a particularly preferred rate is 400 g ai/ha.

Examples of crops include monocotyledon crops such as cereal crops (such as wheat, millet, sorghum, rye, triticale, oats, barley, teff, spelt, buckwheat, fonio and quinoa), rice, sugar cane, and/or corn (maize); and dicotyledon crops such as beet (such as sugar beet or fodder beet); fruits (such as pomes, stone fruits or soft fruits, for example apples, pears, plums, peaches, almonds, cherries, strawberries, raspberries or blackberries); leguminous plants (such as beans, lentils, peas or soybeans); oil plants (such as rape, mustard, poppy, olives, sunflowers, coconut, castor oil plants, cocoa beans or groundnuts); cucumber plants (such as marrows, cucumbers or melons); fibre plants (such as cotton, flax, hemp or jute); citrus fruit (such as oranges, lemons, grapefruit or mandarins); vegetables (such as spinach, lettuce, cabbages, carrots, tomatoes, potatoes, cucurbits or paprika); lauraceae (such as avocados, cinnamon or camphor); tobacco; nuts; coffee; tea; vines; hops; durian; bananas; natural rubber plants; and ornamentals (such as flowers, shrubs, broad-leaved trees or evergreens, for example conifers). This list does not represent any limitation.

Crops include those that have been rendered tolerant to herbicides like bromoxynil or classes of herbicides (such as HPPD inhibitors, ALS inhibitors (for example primisulfuron, prosulfuron and trifloxysulfuron), EPSPS (S-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LiberyLink®. Crops also includes plants that have been transformed by the use of recombinant DNA techniques so that they are capable of synthesising one or more selectively acting toxins, such as are known, for example, from toxin-producing bacteria, especially those of the genus *Bacillus*. Crops also includes plants which have been transformed by the use of recombinant DNA techniques so that they are capable of synthesising antipathogenic substances having a selective action, such as, for example, the so-called "pathogenesis-related proteins". Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

In particular, the method of the present invention may be applied to crops selected from the list consisting of cereals, sugar cane, rice and corn. Suitably, the crop plants are cereal crops. More suitably, they are wheat or barley. In one embodiment, the cereal crop is wheat. In a further embodiment, the cereal crop is barley. In a further embodiment, the crop plants are rice plants. In a further embodiment, the crop plants are sugar cane plants. In further embodiment, the crop plants are corn plants. In one embodiment, the crop is not turfgrass.

The plant growth regulator and jasmonic acid of the present invention may be applied either simultaneously or sequentially in any order. If administered sequentially, the components may be administered in any order in a suitable timescale, for example, with no longer than 1 month, no longer than 1 week, or no longer than 24 hours between the time of administering the first component and the time of administering the last component. Suitably, the components are administered within a timescale of a few hours, such as one hour. If the plant growth regulator and jasmonic acid components are administered simultaneously, they may be administered separately or as a tank mix or as a pre-formulated mixture. In one embodiment the mixture or composition of the present invention may be applied to the crop plants as a seed treatment prior to planting.

When the method of the present invention refers to the application to crop plants of a co-formulated composition, the composition comprises both plant growth regulator and jasmonic acid. The compounds may be homogeneously mixed together with other formulation components necessary to make the desired formulation type, as is known to those skilled in the art.

In one embodiment of the present invention, the plant growth regulator and jasmonic acid or salt or ester thereof, are applied in the form of a composition comprising an agriculturally acceptable carrier.

The compounds of the present invention may be used in unmodified form, but are generally formulated into compositions using formulation adjuvants, such as carriers, solvents and surface-active substances. The formulations can be in various physical forms, for example dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oil dispersions, suspoemulsions, capsule suspensions, emulsifiable granules, soluble liquids, water-soluble concentrates (with water or a water-miscible organic solvent as carrier), or impregnated polymer films. Such formulations can either be used directly or are diluted prior to use. Diluted formulations can be prepared, for example, with water, liquid fertilizers, micro-nutrients, biological organisms, oil or solvents. These formulations may contain as little as about 0.5% to as much as about 95% or more by weight of active ingredient. The optimum amount for any given compound will depend on formulation, application equipment and nature of the plants to be controlled.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles and are usually applied without dilution to the area in which suppression of vegetation is desired. Typical carriers for granular formulations include fertiliser, sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Particularly suitable is a fertiliser granule carrier. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins. The granular substrate material can be one of the typical carriers mentioned above and/or can be a fertiliser material e.g. urea/formaldehyde fertilisers, ammonium, liquid nitrogen, urea, potassium chloride, ammonium compounds, phosphorus compounds, sulphur, similar plant nutrients and micronutrients and mixtures or combinations thereof. The plant growth regulator and jasmonic acid may be homogeneously distributed throughout the granule or may be spray impregnated or absorbed onto the granule substrate after the granules are formed.

Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule and may include solvent in addition to the active compound.

Other useful formulations for plant growth regulation applications include simple solutions of the active ingredients in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Many of the formulations described above include wetting, dispersing or emulsifying agents. Examples are alkyl and alkylaryl sulphonates and sulphates and their salts, polyhydric alcohols; polyethoxylated alcohols, esters and fatty amines. These agents, when used, normally comprise from 0.1% to 15% by weight of the formulation.

Suitable agricultural adjuvants and carriers, either formulated together and/or added separately, that are useful in formulating the compositions of the invention in the formulation types described above are well known to those skilled in the art. Suitable examples of the different classes are found in the non-limiting list below.

Liquid carriers that can be employed include water, toluene, xylene, petroleum naphtha, crop oils, AMS; acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc. ethylene glycol, propylene glycol, glycerine, N-methyl-2-pyrrolidinone, and the like. Water is generally the carrier of choice for the dilution of concentrates.

Suitable solid carriers include talc, titanium dioxide, pyrophyllite clay, silica, attapulgite clay, kieselguhr, chalk, diatomaxeous earth, lime, calcium carbonate, bentonite clay, fuller's earth, fertiliser, cotton seed hulls, wheat flour, soybean flour, pumice, wood flour, walnut shell flour, lignin and the like.

A broad range of surface-active agents are advantageously employed in both said liquid and solid compositions, especially those designed to be diluted with carrier before application. The surface-active agents can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants, sticking agents, and the like. The compositions can also be formulated with liquid fertilizers or solid, particulate fertiliser carriers such as ammonium nitrate, urea and the like.

Also, the present invention may optionally include one or more additional pesticides such as insecticides, nematicides, fungicides or herbicides or additional plant growth regulators. Co-application of pesticides with the present invention has the added benefit of minimising farmer time spent applying products to crops, since only a single application may be required to both provide growth regulation and control pests.

According to the present invention, there is provided the use of a composition comprising a synergistically effective amount of a plant growth regulator and jasmonic acid or a salt or ester thereof, for regulating the growth of and/or enhancing crop plants, as described above. Suitably, the crop plants are cereals, sugar cane, rice or corn.

Compositions of the present invention may contain from about 0.001% to about 99% by weight active ingredients. Suitably, the composition contains from about 0.001% to about 50% by weight active ingredients. More suitably, the composition contains from about 0.001% to about 10% by weight active ingredients. More suitably, the composition contains from about 0.001% to about 1% by weight active ingredients. If the formulation is in the form of a concentrate, requiring dilution with water before use, it will contain a higher amount of active ingredients than a composition that is ready to use without dilution.

The following examples further exemplify the present invention. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the attached claims.

EXAMPLES

Example 1

A glasshouse trial was setup to compare growth regulation effects of trinexapac-ethyl, methyl jasmonate, and mixtures of trinexapac-ethyl and methyl jasmonate at various rates, on both winter and summer varieties of barley and wheat (summer barley Pasadena, winter barley Hasso, winter wheat Arina, and summer wheat Lona).

Table 1 describes the treatments made. Each treatment was applied as a spray to the leaves of the plant at plant growth stage 30 (start of stem elongation). Assessments of growth were made two weeks after application, and the results are expressed as percentage growth reduction in table 2.

TABLE 1

Treatment list

| Treatment Number | Treatment description | Treatment details | Rate (g AI/ha) |
|---|---|---|---|
| 1 | Trinexapac-ethyl (TXP) only | Moddus ® | 100 |
| 2 | TXP only | Moddus ® | 50 |
| 3 | Methyl jasmonate only (m-JA) | Methyl jasmonate | 400 |
| 4 | m-JA only | Methyl jasmonate | 200 |
| 5 | m-JA only | Methyl jasmonate | 100 |
| 6 | TXP + m-JA | Moddus ® + m-JA | 100 + 400 |
| 7 | TXP + m-JA | Moddus ® + m-JA | 50 + 400 |
| 8 | TXP + m-JA | Moddus ® + m-JA | 50 + 200 |

TABLE 2

Results

| | Summer-Barley Pasadena | | Winter-Barley Hasso | | Winter-Wheat Arina | | Summer-Wheat Lona | |
|---|---|---|---|---|---|---|---|---|
| Treatment | % growth reduction (actual) | Colby (expected) | % growth reduction (actual) | Colby (expected) | % growth reduction (actual) | Colby (expected) | % growth reduction (actual) | Colby (expected) |
| 1 | 0 | n/a | 8 | n/a | 10 | n/a | 5 | n/a |
| 2 | 0 | n/a | 3 | n/a | 5 | n/a | 3 | n/a |
| 3 | 0 | n/a | 3 | n/a | 0 | n/a | 3 | n/a |
| 4 | 0 | n/a | 0 | n/a | 0 | n/a | 0 | n/a |
| 5 | 0 | n/a | 0 | n/a | 0 | n/a | 0 | n/a |
| 6 | 13 | 0 | 20 | 10 | 20 | 10 | 25 | 7 |
| 7 | 10 | 0 | 20 | 5 | 25 | 5 | 20 | 5 |
| 8 | 5 | 0 | 5 | 3 | 10 | 5 | 13 | 3 |

Shading/bold type indicates synergy (i.e. where the actual percentage growth reduction observed is greater than the 'Colby' expected growth reduction).

A synergistic growth reduction effect was observed when applying mixtures of trinexapac-ethyl and methyl jasmonate, at all rates tested, and against all 4 species.

The invention claimed is:

1. A method for regulating the growth of and/or enhancing crop plants, comprising applying to the plants, plant parts, plant propagation material, or a plant growing locus, a plant growth regulator and jasmonic acid or a salt or methyl ester thereof, wherein the crop plants are cereals, rice or corn, and wherein the plant growth regulator is trinexapac-ethyl; wherein the trinexapac-ethyl and the jasmonic acid or a salt or methyl ester thereof, are applied in a synergistically effective amount.

2. A method according to claim 1, wherein the jasmonic acid is in the form of methyl jasmonate.

3. A method according to claim 1, wherein the crop plants are cereals.

4. A method according to claim 1, wherein the plant growth regulator and the jasmonic acid or a salt or methyl ester thereof, are applied in the form of a composition comprising an agriculturally acceptable carrier.

5. A method according to claim 1, wherein the plant growth regulator and the jasmonic acid are applied to the plant in a weight ratio from about 1:1 to about 1:10.

6. A method according to claim 1, wherein the plant growth regulator is applied at a rate from about 50 to about 100 g ai/ha.

7. A method according to claim 1, wherein the jasmonic acid is applied at a rate from about 100 to about 400 g ai/ha.

8. A method according to claim 1, wherein the regulating includes enhancing wherein the enhancing is improved plant yield.

9. A method according to claim 1, wherein the regulating includes enhancing wherein the enhancing is improved plant vigour and/or plant tolerance to stress factors.

10. A method according to claim 9, wherein the regulating includes enhancing wherein the enhancing is improved tolerance to drought conditions.

11. A method for regulating the growth of crop plants and/or enhancing crop plants, wherein the crop plants are chosen from at least one of a cereal, rice and corn, the method comprising:

applying a synergistically effective amount of a plant growth regulator and jasmonic acid or a salt or methyl ester thereof to the plants, plant parts, plant propagation material, or a plant growing locus, wherein the plant growth regulator is trinexapac-ethyl.

* * * * *